US010426916B2

(12) United States Patent
Sakai

(10) Patent No.: US 10,426,916 B2
(45) Date of Patent: Oct. 1, 2019

(54) METHOD OF USING AUTONOMIC NERVE FLUCTUATIONS AND SYSTEM USING THE SAME

(71) Applicant: Panasonic Intellectual Property Management Co., Ltd., Osaka (JP)

(72) Inventor: Masahiro Sakai, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 292 days.

(21) Appl. No.: 15/441,313

(22) Filed: Feb. 24, 2017

(65) Prior Publication Data

US 2017/0259030 A1    Sep. 14, 2017

(30) Foreign Application Priority Data

Mar. 10, 2016   (JP) .................................. 2016-047328

(51) Int. Cl.
*A61M 21/02*    (2006.01)
*A61B 3/00*    (2006.01)
(Continued)

(52) U.S. Cl.
CPC ........... *A61M 21/02* (2013.01); *A61B 3/0025* (2013.01); *A61B 3/1005* (2013.01); *A61B 3/112* (2013.01); *A61B 5/0402* (2013.01); *A61B 5/04012* (2013.01); *A61B 5/1104* (2013.01); *A61B 5/163* (2017.08); *A61B 5/4035* (2013.01);
(Continued)

(58) Field of Classification Search
CPC ..... A61B 5/4035; A61B 5/486; A61B 3/0025; A61B 3/0091; A61B 3/112; A61B 3/14; A61B 5/0245; A61B 5/04012; A61B 5/163; A61M 2021/0044; A61M 21/02
See application file for complete search history.

(56) References Cited

U.S. PATENT DOCUMENTS

2012/0277521 A1*  11/2012  Chamberlin .......... A61M 21/02
                                                      600/28

FOREIGN PATENT DOCUMENTS

JP    2001-252265    9/2001
JP    2008-125802    6/2008

OTHER PUBLICATIONS

Masahito Sakakibara et al., "Heart rate variability biofeedback", Japanese Journal of Biofeedback Research, vol. 40, Issue 2, 43-46, 2013.

(Continued)

*Primary Examiner* — Christine H Matthews
(74) *Attorney, Agent, or Firm* — Greenblum & Bernstein, P.L.C.

(57) ABSTRACT

A method comprising: (a) obtaining information about a period of a fluctuation cycle in an autonomic nerve of a user; and (b) repeating, in a same period as the period of the fluctuation cycle in the autonomic nerve, a process that includes inducing a point of gaze of the user to move in a direction away from the user and inducing the point of gaze of the user to move in a direction to approach the user, according to the obtained information. The period of the fluctuation cycle in the autonomic nerve is a period of a fluctuation cycle in a diameter of a pupil of the user, a period of a fluctuation cycle in a heart beat of the user, or a period calculated from the period of the fluctuation cycle in the diameter of the pupil and the period of the fluctuation cycle in the heart beat.

17 Claims, 12 Drawing Sheets

(51) Int. Cl.

| | |
|---|---|
| *A61B 3/10* | (2006.01) |
| *A61B 5/04* | (2006.01) |
| *A61B 5/0402* | (2006.01) |
| *A61B 5/00* | (2006.01) |
| *A61B 5/11* | (2006.01) |
| *A61B 5/16* | (2006.01) |
| *A61M 21/00* | (2006.01) |
| *A61B 3/11* | (2006.01) |
| *A61B 3/14* | (2006.01) |

(52) U.S. Cl.
CPC ............ *A61B 5/486* (2013.01); *A61B 5/6801* (2013.01); *A61M 21/00* (2013.01); *A61B 3/0091* (2013.01); *A61B 3/14* (2013.01); *A61B 5/1107* (2013.01); *A61B 5/1128* (2013.01); *A61M 2021/0005* (2013.01); *A61M 2021/0044* (2013.01); *A61M 2230/06* (2013.01)

(56) References Cited

OTHER PUBLICATIONS

Inger Ekman et al., "Voluntary Pupil Size Change as Control in Eyes Only Interaction", proceedings of the 2008 symposium on Eye tracking research & applications, 115-118, Mar. 26, 2008.

\* cited by examiner

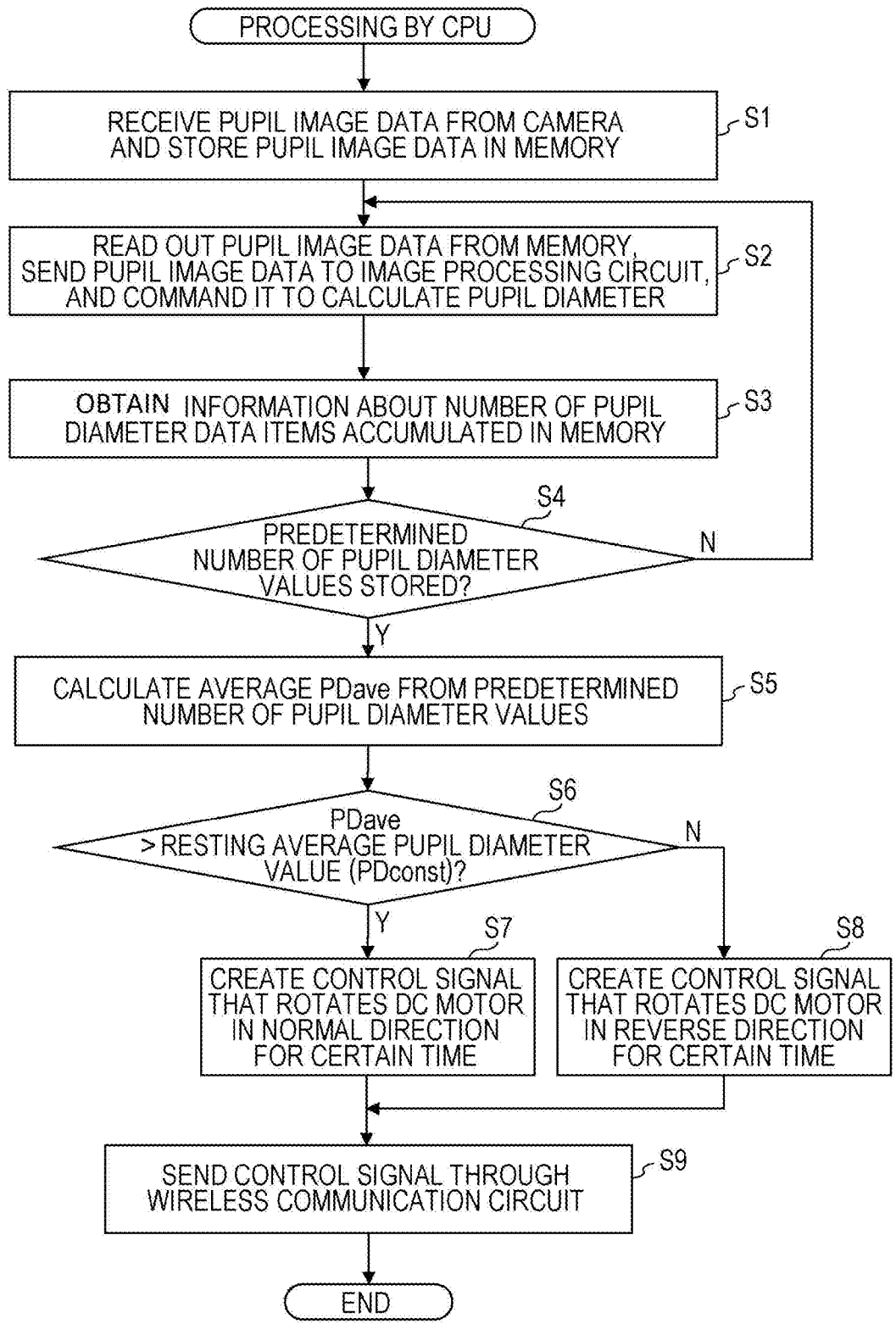

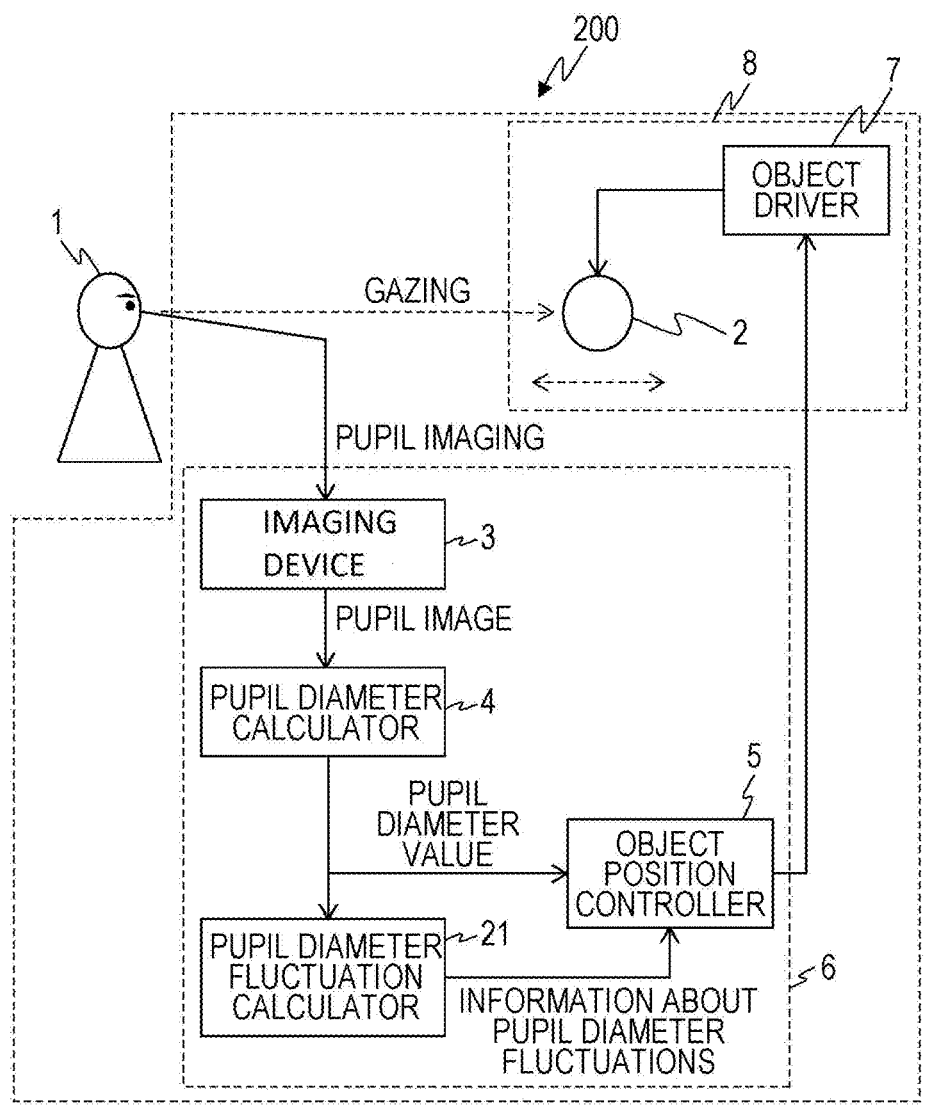

METHOD OF USING AUTONOMIC NERVE FLUCTUATIONS AND SYSTEM USING THE SAME

BACKGROUND

1. Technical Field

The present disclosure relates to a method of using autonomic nerve fluctuations and a system that uses these fluctuations.

2. Description of the Related Art

Biofeedback technology is under study in recent years. Biofeedback refers to technology or a phenomenon that enables the state in the body of a person to be consciously adjusted by feeding back information of which the person is not aware in an engineering way so that the person becomes aware of the information. For example, a stimulus that generates a physiological state homogeneous to a target physiological state of a test subject is applied to the test subject in consideration of the current heart rate, pulse rate, breathing rate, and other bio-information of the test subject. Therefore, the current physiological state of the test subject can be alleviated, and the test subject can be gradually induced to the target physiological state.

Conventional known biofeedback apparatuses are described in, for example, Japanese Unexamined Patent Application Publication Nos. 2008-125802 and 2001-252265.

Japanese Unexamined Patent Application Publication No. 2008-125802 discloses a technology by which biofeedback is performed by using a heart rate, myoelectricity, a blood pressure, a breathing rate, galvanic skin reflex, and the like. FIG. 11 illustrates a conventional biofeedback apparatus 600 described in Japanese Unexamined Patent Application Publication No. 2008-125802. A physiological measurer 63 in the biofeedback apparatus 600 obtains physiological information from a test subject (sometimes referred to as the user). The obtained information is sent to a state inferrer 64, which calculates an autonomic nerve activity index, after which the obtained information is transferred to a state determiner 65 and a control determiner 66 in that order. Finally, a stimulus presenter 68 presents some kind of stimulus to the user. In an embodiment in Japanese Unexamined Patent Application Publication No. 2008-125802, known heart rate variability biofeedback is used (see M. Sakakibara, P. Lehrer, "Heart rate variability biofeedback", Japanese Journal of Biofeedback Research, Vol. 40, Issue 2, 43-46 (2013), for example).

Japanese Unexamined Patent Application Publication No. 2001-252265 discloses a technology by which biofeedback is performed by using brain waves (or magnetoencephalography), biochemical reactions, a wink frequency, a skin resistance, sweating, voice intonation, body motion, mouse motion, dryness, head motion, a pupil size, facial expressions, a heart rate, a pulse rate, a breathing rate, a breathing state, and a body surface temperature. In Japanese Unexamined Patent Application Publication No. 2001-252265, the metal activity of the user is inferred by using the above information, and stimuli with intensities that are changed with time are applied to the five senses of the user by using a 1/f fluctuation theory or the like. FIG. 12 illustrates a conventional biofeedback apparatus described in Japanese Unexamined Patent Application Publication No. 2001-252265. A mental activity detector 71 detects various biological reactions of the user. A mental activity determiner 76 comprehensively analyzes the detection results. As a result, the mental activity state of the user is determined. A stimulus generator 73 applies stimuli having a time-varying intensity to the five senses of the user so as to attain the mental activity selected by a mental activity selector 74 as a target.

SUMMARY

One non-limiting and exemplary embodiment provides a method of using autonomic nerve fluctuations in a simple manner.

In one general aspect, the techniques disclosed here feature a method that includes: (a) obtaining information about a period of a fluctuation cycle in an autonomic nerve of a user; and (b) repeating, in a same period as the period of the fluctuation cycle in the autonomic nerve, a process that includes inducing a point of gaze of the user to move in a direction away from the user and inducing the point of gaze of the user to move in a direction to approach the user, according to the obtained information. The period of the fluctuation cycle in the autonomic nerve is a period of a fluctuation cycle in a diameter of a pupil of the user, a period of a fluctuation cycle in a heart beat of the user, or a period calculated from the period of the fluctuation cycle in the diameter of the pupil and the period of the fluctuation cycle in the heart beat.

In the method in one exemplary embodiment in the present disclosure, autonomic nerve fluctuations can be used in a simple manner.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 4 is a flowchart indicating a procedure for processing executed by a CPU that operates as an implementation of a pupil diameter calculator and an object position controller;

FIG. 7 schematically illustrates the structure of a biofeedback system in a second embodiment;

DETAILED DESCRIPTION

Figure 1:
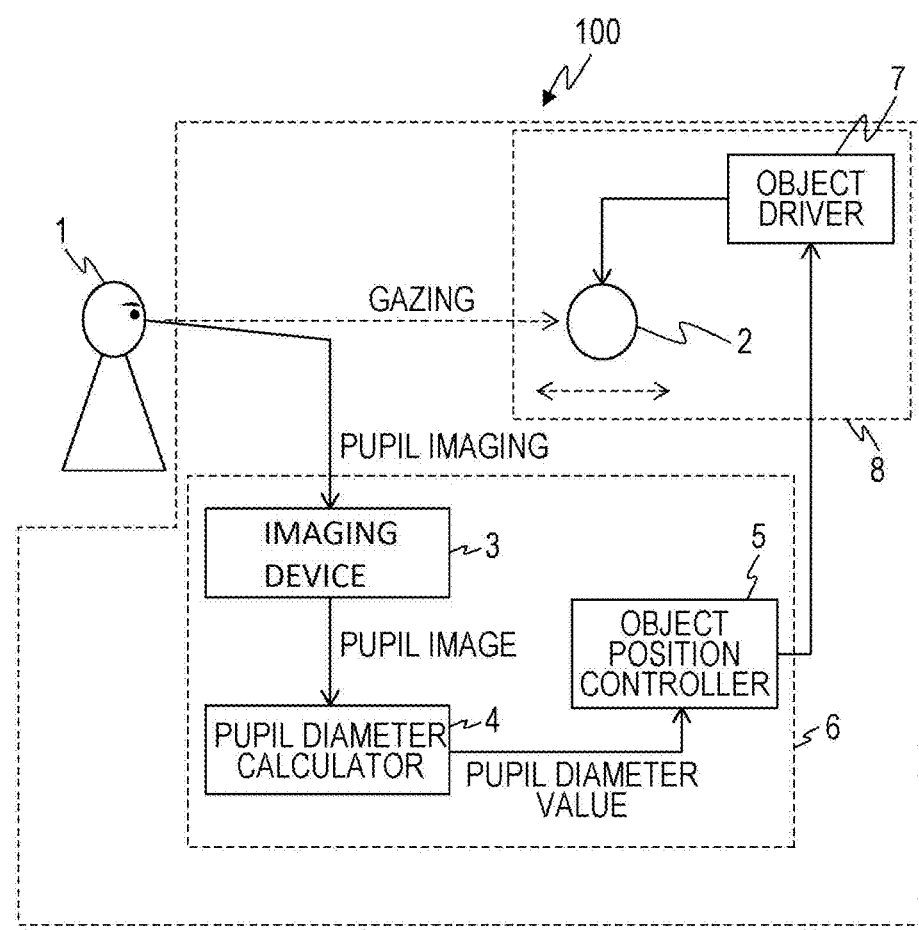
FIG. 1 schematically illustrates the structure of a biofeedback system in a first embodiment.

Findings on which the present disclosure is based will be described first.

In biofeedback technology, the physiological state of a person is controlled by feeding back information of which a person is not aware in an engineering way so that the person becomes aware of the information. In Japanese Unexamined Patent Application Publication No. 2008-125802, virtually only heart beats are specifically described as physiological information. The technology described therein is the same as the technology described in "Heart rate variability biofeedback" as referred to above. In heart rate variability biofeedback, heart beats are controlled by slow diaphragmatic breathing. A study by the present inventor indicates that some users are not good at consciously performing slow diaphragmatic breathing. Even if a user can perform slow diaphragmatic breathing in a normal state, the user may not easily perform slow diaphragmatic breathing when, for example, the user is under strong stress. That is, there is case in which it is effectively difficult to perform heart rate variability biofeedback.

Although Japanese Unexamined Patent Application Publication No. 2001-252265 includes many descriptions of physiological information, they are generally known and specific embodiments are not included. In addition, although Japanese Unexamined Patent Application Publication No. 2001-252265 mainly proposes blinking of light having 1/f fluctuations and sounds as a feedback method, whether effects of feedback are exerted on obtained physiological information is neither verified nor confirmed; this is a matter of speculation.

After a diligent study, the present inventor found that when biofeedback is performed by using pupil diameter fluctuations, it is possible to perform more effective biofeedback more easily.

As described above, in general biofeedback, a desired physiological state is induced by applying stimuli to a user to change the user's autonomic nerves. The autonomic nerves are composed of two nerves, sympathetic nerve and parasympathetic nerve. Since the sympathetic nerve and parasympathetic nerve complementarily work, the functions of organs and regions are automatically adjusted, regardless of the intention of the user. This is called double domination by the autonomic nerves. Unbalance between the sympathetic nerve and the parasympathetic nerve leads to a disease.

"Heart rate variability biofeedback" referred to above discloses heart rate variability biofeedback, which is typical biofeedback. In heart rate variability biofeedback, heart beats are accessed through diaphragmatic breathing to adjust the autonomic nerves. Specifically, the user is made to intentionally breathe slowly so that variations in breathing are synchronized with periodic variations in blood pressure to achieve the maximum fluctuation in heart beats. Periodic variations in blood pressure (that is, periodic variations in a baroceptor at an end) form a low-frequency component in heart beat fluctuations; periodic variations in blood pressure are generally 0.04 to 0.15 Hz. Variations in breathing form a high-frequency component in heart beat fluctuations; variations in breathing are generally 0.15 to 0.50 Hz.

On the analogy of the above, the present inventor thought that application to biofeedback is possible if the following conditions are met: a physiological signal (1) which is dominated by the autonomic nerves, (2) intentional intervention of which is possible in some methods, and (3) which can be measured comparatively easily is present.

As a fact related to condition (1) above, it is known that the pupil diameter is dominated by the autonomic nerves, pupil diameter fluctuations are present, and there are a low-frequency component and a high-frequency component. When a pupil image is obtained with a near-infrared lamp and a camera, and is binarized, the pupil diameter can be easily calculated as a measureable physiological signal in condition (3).

According to a study by the present inventor, it was clarified that the pupil diameter can be intentionally changed periodically by a convergence reaction caused by simple training. That is, it was clarified that condition (2) can be satisfied. Specifically, it was found that when the user is made to gaze at a predetermined object in a relaxed manner, convergence reflection can be periodically induced by periodically changing the distance between the object and the user. Convergence reflection is a series of reactions in which, when a person gazes at an approaching object, the medial rectus muscles of both eyes contract and the visual axes of both eyes come close to each other, at which time the pupils contract. Since the user only needs to gaze at the object, biofeedback in which pupil diameter fluctuations are used is much easier than heart rate variability biofeedback in which diaphragmatic breathing needs to be mastered.

According to a further study by the present inventor, it was found that when pupil diameter fluctuations are used, at least conditions (1) and (2) of conditions (1) to (3) are satisfied, biofeedback can be achieved. That is, it was found that the period of the autonomic nerves can be controlled just by, for example, moving an object from a near position to a far position and from a far position to a near position so as to synchronize with the period of the fluctuation cycle in the autonomic nerves of the user, the period having been obtained in advance. Once the period of the fluctuation cycle in the autonomic nerves of the user is obtained, the pupil diameter does not need to be measured to obtain a physiological signal. The user only needs to gaze at the object, so a facility that measures the pupil diameter is not needed. In addition, biofeedback in which pupil diameter fluctuations are used is much easier than heart rate variability biofeedback in which diaphragmatic breathing needs to be mastered. As described above, the present inventor developed a technology by which the same effect as in the conventional heart rate variability biofeedback methods can be obtained by a structure and/or method that is easier, simpler, and more practical than when the conventional heart rate variability biofeedback methods are used.

A method in one aspect of the present disclosure includes (a) obtaining information about a period of a fluctuation cycle in an autonomic nerve of a user; and (b) repeating, in a same period as the period of the fluctuation cycle in the autonomic nerve, a process that includes inducing a point of gaze of the user to move in a direction away from the user and inducing the point of gaze of the user to move in a direction to approach the user, according to the obtained information. The period of the fluctuation cycle in the autonomic nerve is a period of a fluctuation cycle in a diameter of a pupil of the user, a period of a fluctuation cycle in a heart beat of the user, or a period calculated from the period of the fluctuation cycle in the diameter of the pupil and the period of the fluctuation cycle in the heart beat.

The period of the fluctuation cycle in the autonomic nerves may be the period of the fluctuation cycle in the diameter of the pupil.

The period of the fluctuation cycle in the diameter of the pupil may be a period corresponding to a peak frequency in a predetermined frequency band included in fluctuations in the diameter of the pupil of the user at rest.

The period of the fluctuation cycle in the autonomic nerves may be the period of the fluctuation cycle in heart beats.

The period of the fluctuation cycle in heart beats may be a period corresponding to a peak frequency in a predetermined frequency band included in fluctuations in heart beats of the user at rest.

In step (b) above, the repeating of the process may include step (b1) of adjusting the point of gaze of the user to an object by having the user gaze at the object and step (b2) of alternately repeating, after step (b1) above, motion of the object in a direction away from the user and motion of the object in a direction to approach the user.

In step (b) above, the repeating of the process may include step (b1) of displaying a three-dimensional image of an object on the screen of a display device, step (b2) of adjusting the point of gaze of the user to the object by having the user gaze at the object, and step (b3) of alternately repeating, after step (b2) above, virtual motion of the object in a direction away from the user and virtual motion of the object in a direction to approach the user by changing the size of the object.

In step (b) above, the repeating of the process may include step (b1) of adjusting the point of gaze of the user to a position illuminated by light by having the user gaze at the position illuminated by the light and step (b2) of alternately repeating, after step (b1) above, movement of the position illuminated by the light in a direction away from the user and movement of the position illuminated by the light in a direction to approach the user.

In step (b) above, the repeating of the process may include step (b1) of placing a first lamp and a second lamp at positions apart from the user by different distances, step (b2) of turning on the first lamp or the second lamp and adjusting the point of gaze of the user to the lamp that is turned on by having the user gaze at the lamp that is turned on, and step (b3) of alternately turning on, after step (b2) above, the first lamp and the second lamp.

The method may include step (c) of photographing the pupil of the user while performing step (b) and calculating the value of the diameter of the pupil of the user from one or a plurality of images obtained by photography and step (d) of adjusting, according to the calculated value, a range within which the point of gaze of the user moves.

The method may further include a step of preparing, before step (b), a target value of the diameter of the pupil, and step (d) may include step (d1) of, if the calculated value of the diameter of the pupil is larger than the target value, inducing the point of gaze of the user to move in a direction to approach the user and/or, if the calculated value of the diameter of the pupil is smaller than the target value, inducing the point of gaze of the user to move in a direction away from the user.

A system in one aspect of the present disclosure includes: a storage device that holds information about a period of a fluctuation cycle in an autonomic nerve of a user; and a controller that repeats, in a same period as the period of the fluctuation cycle in the autonomic nerve, a process that includes inducing a point of gaze of the user to move in a direction away from the user and inducing the point of gaze of the user to move in a direction to approach the user, according to a control signal based on the information held in the storage device. The period of the fluctuation cycle in the autonomic nerve is a period of a fluctuation cycle in a diameter of a pupil of the user, a period of a fluctuation cycle in a heart beat of the user, or a period calculated from the period of the fluctuation cycle in the diameter of the pupil and the period of the fluctuation cycle in the heart beat.

The system may further include: an image processing circuit that calculates a plurality of values of the diameter of the pupil from a plurality of images obtained by photographing the pupil of the user; and a processor that calculates the period of the fluctuation cycle in the diameter of the pupil from the plurality of values of the diameter of the pupil, and stores the information about the period in the storage device.

The system may further include a processor that calculates the period of the fluctuation cycle in the diameter of the pupil from a plurality of images obtained by photographing the pupil of the user and stores the information about the period in the storage device.

The system may further include: an electrocardiograph adapted to be worn on the user, the electrocardiograph that measures an electrocardiographic waveform of the user; and a processor that calculates the period of the fluctuation cycle in heart beats according to the electrocardiographic waveform of the user and stores the information about the period in the storage device.

The system in another aspect of the present disclosure further includes: an object to which the point of gaze of the user is adjusted; a motor that moves the object in a direction away from the user and in a direction to approach the user; and a processor that creates the control signal according to the information held in the storage device. The controller may move, in a same period as the period of the fluctuation cycle in the autonomic nerves, the object by controlling the motor in response to the control signal.

The system may further include: an image processing circuit that calculates a value of the diameter of the pupil from one or more images obtained by photographing the pupil of the user while the point of gaze of the user is being induced by the controller; and a processor. The storage device may further store a target value of the diameter of the pupil. The processor may compare the calculated value of the diameter of the pupil with the target value; if the calculated value of the diameter of the pupil is larger than the target value, the processor creates the control signal to induce the point of gaze of the user to move in a direction to approach the user; if the calculated value of the diameter of the pupil is smaller than the target value, the processor creates the control signal to induce the point of gaze of the user to move in a direction away from the user. The controller may induce the point of gaze of the user in response to the control signal.

The system may further include a processor that calculates a value of the diameter of the pupil from one or more images obtained by photographing a pupil of the user while the point of gaze of the user is being induced by the controller. The storage device may further store a target value of the diameter of the pupil. The processor may compare the calculated value of the diameter of the pupil with the target value; if the calculated value of the diameter of the pupil is larger than the target value, the processor creates the control signal to induce the point of gaze of the user to move in a direction to approach the user; if the calculated value of the diameter of the pupil is smaller than the target value, the processor creates the control signal to induce the point of gaze of the user to move in a direction away from the user. The controller may induce the point of gaze of the user in response to the control signal.

Embodiments of the biofeedback apparatus in the present disclosure will be described with reference to the attached drawings. First to third embodiments described below are respectively related to a biofeedback apparatus when conditions (1) to (3) described above are satisfied. A fourth embodiment is related to a biofeedback apparatus when conditions (1) and (2) above are satisfied.

First Embodiment

FIG. 1 schematically illustrates the structure of a biofeedback system 100 in this embodiment. For easy understanding, a user 1 is also illustrated. The biofeedback system 100 will be outlined first.

In the biofeedback system 100, the user 1 is commanded to gaze at an object 2. The biofeedback system 100 identifies the size of the diameter of a current pupil of the user 1. If the identified size of the diameter of the pupil is larger than a reference, the object 2 is moved close to the user 1 so that the diameter of the pupil is reduced. If the identified size is smaller than the reference, the object 2 is moved away from the user 1 so that the diameter of the pupil is enlarged. The reference may vary with the user. In this embodiment, the average diameter of the pupil of the user 1 at rest (the average will be referred to below as the at-rest average pupil diameter value) is taken as the reference. Note that "average" in this disclosure includes arithmetic mean. The at-rest average pupil diameter value is obtained in advance from the diameter of the pupil of the user 1 at rest. The at-rest average pupil diameter value is used as the target value of the pupil diameter, which is intended to be controlled.

At that time, the biofeedback system 100 moves the object 2 toward and away from the user 1 in a fixed period rather than an arbitrary period. This fixed period is the period of the fluctuation cycle in the autonomic nerves of the user 1. The fixed period is also obtained in advance while the user 1 is at rest. The identified pupil diameter and at-rest average pupil diameter value described above are compared with each other at timings corresponding to the fixed period (for example, in a period of half the fixed period). Accordingly, the range within which the object 2 moves is adjusted, so the diameter of the pupil of the user 1 periodically changes within a range including the at-rest average pupil diameter value. As described above, the pupil diameter is dominated by the autonomic nerves and fluctuates. In this embodiment, a period at which the diameter of the pupil of the user 1 fluctuates is obtained as the period of the fluctuation cycle in the autonomic nerves at rest.

When the biofeedback system 100 operates as described above, the point of gaze of the user 1 gazing at the object 2 is induced from a near position to a far position and a far position to a near position in the period of the fluctuation cycle in the autonomic nerves at rest. When the point of gaze moves, a convergence reaction is caused, changing the pupil diameter. As a result, it becomes possible to control the period of the autonomic nerves by using the period of the motion of the object 2 to change the pupil diameter dominated by the autonomic nerves.

The period of the fluctuation cycle in the autonomic nerves at rest can also be obtained by using a physiological signal other than the diameter of the pupil of the user 1, such as, for example, heart beat fluctuations.

The structure of the biofeedback system 100, which performs the above processing, will be specifically described below.

The biofeedback system 100 includes a controller 6 and a feedbacker 8. The controller 6 includes an imaging device 3, a pupil diameter calculator 4, and an object position controller 5. The feedbacker 8 includes the object 2 and an object driver 7.

The imaging device 3 photographs the pupil of the user 1 and obtains an image of the pupil. The obtained pupil image of the user 1 is sent to the pupil diameter calculator 4. The pupil diameter calculator 4 calculates the pupil diameter from the pupil image. An algorithm to calculate the pupil diameter is the same as used in a generally available pupil diameter measuring apparatus. Processing will be specifically described later. The calculated pupil diameter value is sent to the object position controller 5.

The object position controller 5 creates a control signal that controls the position of the object 2, which is movable, according to the pupil diameter value received from the pupil diameter calculator 4, and outputs the created control signal to the feedbacker 8. The object driver 7 in the feedbacker 8 drives the object 2 in response to the control signal received from the object position controller to changes the position of the object 2 to a position identified by the control signal.

For convenience in this description, it will sometimes be represented that the object position controller 5 moves the object 2. In practice, however, the object driver 7 changes the position of the object 2; specifically, the object driver 7 receives a control signal from the object position controller 5 and drives the object 2 in response to the control signal. Since the object position controller 5 performs essential processing to determine the position of the object 2, it will sometimes be represented with attention focused on the essence that the object position controller 5 moves the object 2.

To change the position of the object 2 implies to change the distance between the user 1 and the object 2. When the distance between the object 2 and the user 1 is shortened, the pupil diameter is reduced. By contrast, when the distance between the object 2 and the user 1 is prolonged, the pupil diameter is increased. When reducing the diameter of the pupil of the user 1, the object position controller 5 controls the object 2 so that it moves toward the user 1. When increasing the diameter of the pupil of the user 1, the object position controller 5 controls the object 2 so that it moves away from the user 1.

In this embodiment, the object position controller 5 determines whether to move the object 2 toward or away from the user 1, according to a relationship between the current pupil diameter value and the at-rest average pupil diameter value.

Specifically, the object position controller 5 compares the average pupil diameter obtained after biofeedback has started with the at-rest average pupil diameter value obtained in advance. The average pupil diameter obtained after biofeedback has started is the average of a plurality of values of the pupil diameter measured within a term shorter than half the period of the fluctuation cycle in the autonomic nerves at rest (that is, the feedback period). One value of the pupil diameter measured at a point in time after biofeedback has started may be used, instead of the average of the values of the pupil diameter obtained after biofeedback has started.

The object position controller 5 controls the position of the object 2 so that if the average pupil diameter value is smaller than the at-rest average pupil diameter value, the object 2 is moved away from the user 1 and that if the average pupil diameter value is larger than the at-rest average pupil diameter value, the object 2 is moved toward the user 1.

Figure 2:
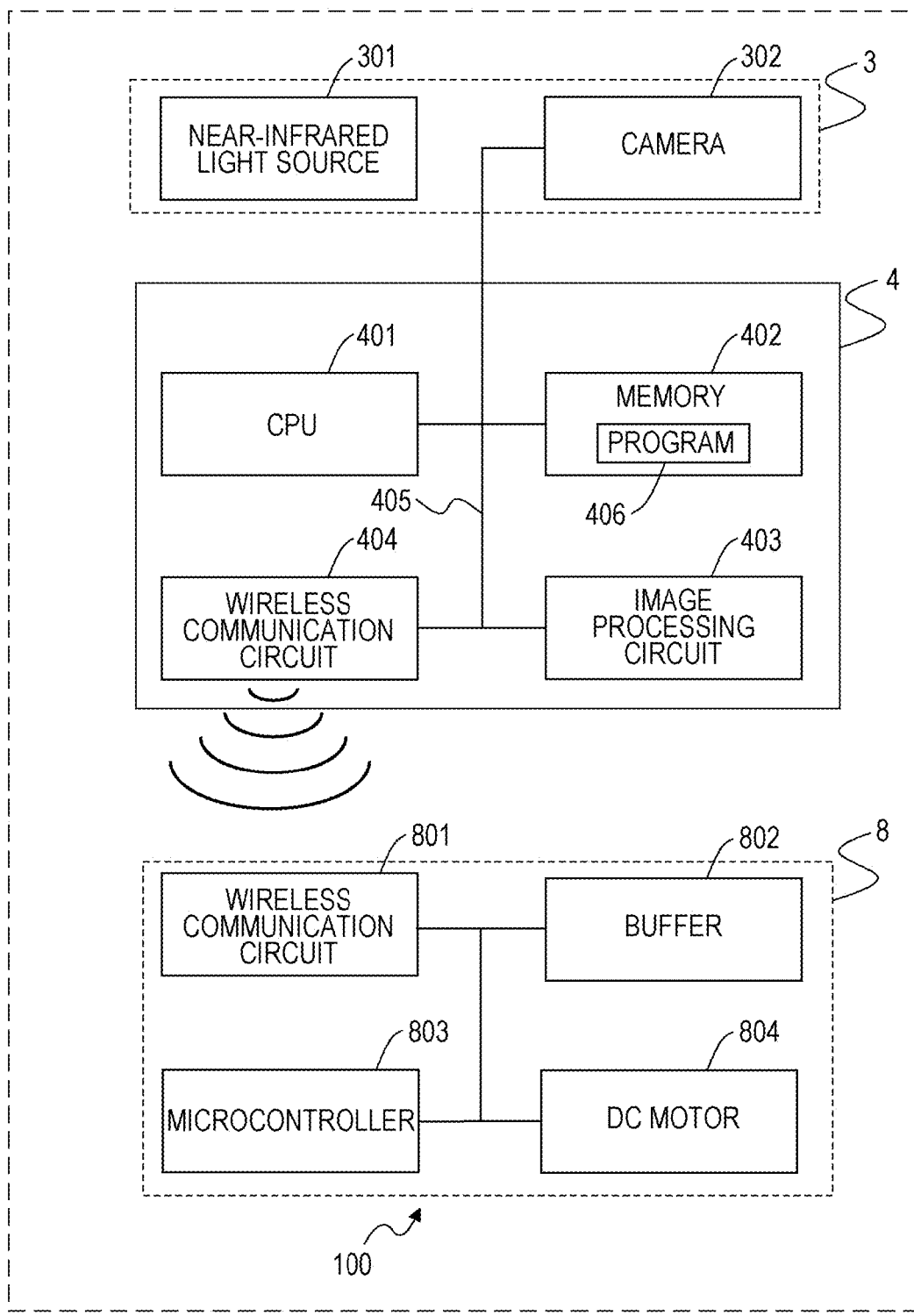
FIG. 2 illustrates an example of the hardware structure of the biofeedback system in the first embodiment.

FIG. 2 illustrates an example of the hardware structure of the biofeedback system 100. In FIG. 2, hardware components corresponding to the imaging device 3, pupil diameter calculator 4, and feedbacker 8 are illustrated. Although a power supply is needed to operate the illustrated hardware components, it is not illustrated.

The imaging device 3 includes, for example, a camera 302. The imaging device 3 may further include a near-infrared light source 301. The near-infrared light source 301 is a light emitting diode (LED) that emits light with a wavelength of, for example, 890 to 940 nm. The camera 302 has sensitivity to the wavelength of the near-infrared light source 301; the camera 302 can take a picture by receiving light with the wavelength. The camera 302 takes a moving picture at, for example, 30 to 300 Hz.

When an eye of the user 1 is photographed by using the above wavelength, even if the iris is dark brown in color and the pupil is black in color, the pupil can be clearly identified.

In the example in FIG. 2, the near-infrared light source 301 has only a function that emits near-infrared light and is not connected to the camera 302. As another example, however, the near-infrared light source 301 may be mounted in the camera 302 and a signal line that can receive a control signal from the camera 302 may be provided so that the near-infrared light source 301 is turned on only in photography.

The pupil diameter calculator 4 is composed of, for example, a signal processing circuit or processor (referred to below as the central processing unit (CPU)) 401, a memory 402, an image processing circuit 403, and a wireless communication circuit 404. These components, which are interconnected with a bus 405, can transmit and receive data among them. The CPU 401 may be operated as the image processing circuit 403 without the image processing circuit 403 being provided.

The CPU 401 executes a computer program 406 stored in the memory 402 and controls the entire operation of the pupil diameter calculator 4. The computer program 406 is a set of commands that execute processing in the flowchart illustrated in FIG. 4.

The image processing circuit 403 is, for example, a graphic processor. In this embodiment, the image processing circuit 403 calculates a pupil diameter from a pupil image by performing processing as described below. First, the image processing circuit 403 binarizes the obtained pupil image. An object of this binarization is to clarify the outline of the pupil.

The image processing circuit 403 applies an ellipse calculation algorithm to the binarized pupil image to identify an ellipse included in the image. The image processing circuit 403 retains the number of pixels corresponding to an ordinary pupil diameter in advance as a threshold. The threshold depends on the number of pixels in the camera 302, the distance between the user 1 and the camera 302, and other factors. A specific example will be described below.

The camera 302 used by the present inventor had 640 pixels vertically by 480 pixels horizontally. The present inventor adjusted the positions of the user 1 and camera 302 so that the whole of one eye of the user 1 is substantially included in the field of view of the camera 302.

Figure 3A:
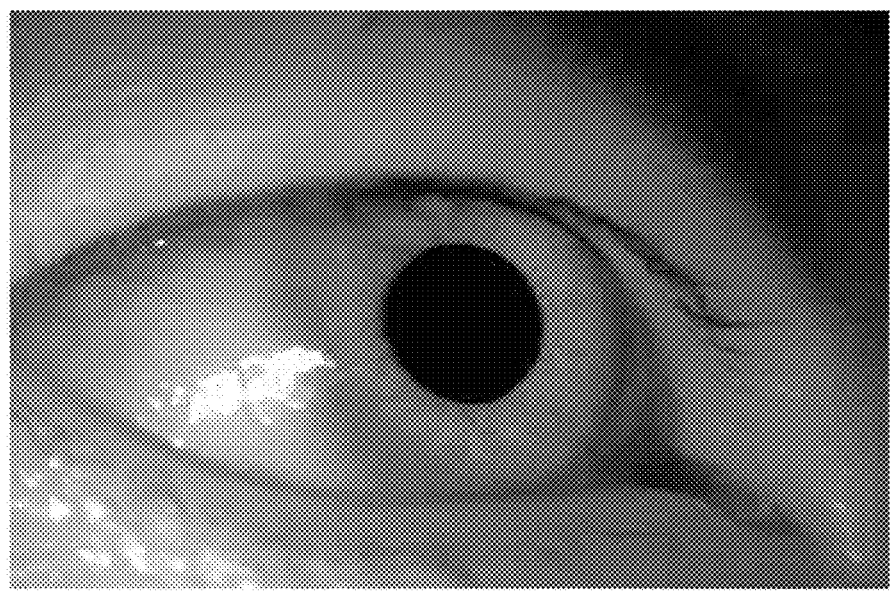
FIG. 3A illustrates an example of a user's eyeball image photographed with a camera.
Figure 3B:
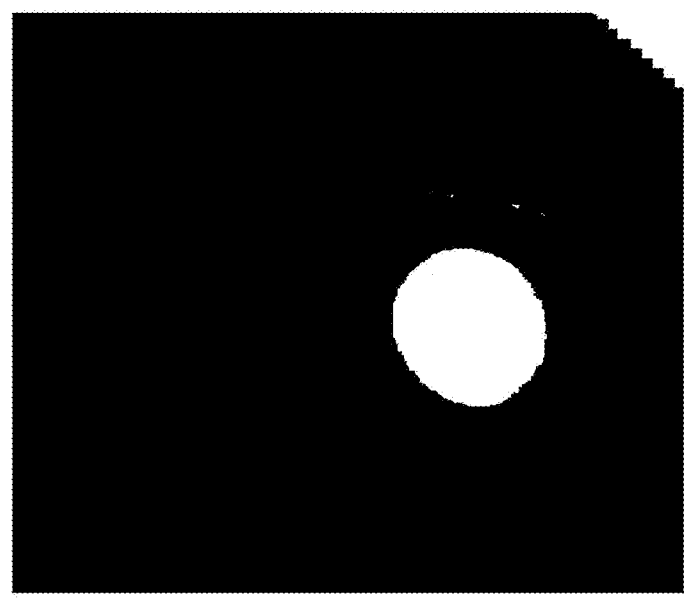
FIG. 3B illustrates part of an image binarized by an image processing circuit.

FIG. 3A illustrates an example of an image of an eyeball of the user 1, the image being captured with the camera 302. FIG. 3B illustrates part of an image binarized by the image processing circuit 403.

In this embodiment, a threshold was set for the brightness of each pixel to perform binarization. In this embodiment, since near-infrared light is emitted for photography, a threshold can be comparatively easily set. Specifically, as is clear from FIG. 3A, the pupil in the captured image is black in color, the iris spreading around the periphery of the pupil is light gray in color, and the outer side of the iris (that is, the tail side of the eye) is white in color. It suffices to set, as a threshold, a value by which each brightness value can be classified as a brightness value corresponding to a black portion of the pupil or another brightness value.

The image processing circuit 403 makes a decision for each pixel in the captured image as to whether the pixel is larger or equal to or smaller than the threshold set for the pixel. If a pixel has a brightness value equal to or smaller than a certain brightness value, the image processing circuit 403 converts the pixel to a white pixel. If the pixel has a brightness value larger than the certain brightness value, the image processing circuit 403 converts the pixel to a black pixel. An image obtained in this way is the image in FIG. 3B. The black pupil in FIG. 3A is represented as a white region in FIG. 3B, and almost all other regions are represented in black. Processing described above is just an example. The pupil may be converted to a black region.

Next, the image processing circuit 403 detects, as a pupil region, a region that is included in the white region in the binarized pupil image (see FIG. 3B) and has a size within a predetermined range. In the experiments carried out by the present inventor, the longer axis of the pupil image was about 20 pixels long in the case of a test subject having a short longer axis and about 150 pixels long in the case of a test subject having a long longer axis; typically (or on the average), the longer axis of the pupil image was about 60 pixels long. The image processing circuit 403 detects, as the pupil region, a white region including a straight line that is, for example, 20 to 150 pixels long. When processing as described above is included, even if an ellipse area is included in a region other than the pupil, it is possible to prevent the region from being decided as the pupil by mistake. In the processing described above, not only an ellipse but also a perfect circle can be detected as a pupil region candidate.

The image processing circuit 403 obtains the length of the longer axis by using, for example, a parallelogram inscribed to the ellipse. The image processing circuit 403 links the midpoints of each two opposing sides of the parallelogram inscribed to the ellipse to obtain two straight lines and identifies the intersection of the two straight lines as the center of the ellipse. The image processing circuit 403 then identifies, as the pupil diameter, the maximum length of line segments, each of which is formed by linking two points on the outline of the ellipse so as to pass through the center of the ellipse.

If near-infrared light emitted from the near-infrared light source 301 is reflected on the cornea at a position near to the pupil, part of the pupil image has high brightness due to reflected light, in which case part of the elliptical region may be lost. The portion having high brightness is called an outlier. The presence of an outliner disables an elliptical region from being detected. However, various technologies to remove an outlier have been developed. Therefore, the removal of an outliner will not be described in this description. It is desirable to remove an outliner before the elliptical region and pupil diameter are detected as described above.

Since the pupil diameter is identified while photography is in progress, the operating frequency when the image processing circuit 403 calculates the pupil diameter is higher than the frequency at which the camera 302 captures an image.

The CPU 401 creates a control signal by using the at-rest average diameter of the pupil of the user 1 and the period of the fluctuation cycle in the autonomic nerves at rest (that is, the feedback period), which are prepared in advance. Information to be used may be stored in a register in the CPU 401 or may be stored in the memory 402.

When pupil diameter values for a predetermined term are accumulated in the memory 402, the CPU 401 calculates the average of these values. The predetermined term used by the present inventor is shorter than half the period of the fluctuation cycle in the autonomic nerves at rest (that is, the feedback period). Specifically, the predetermined term was set to the last quarter of one way from the maximum fluctuation value to the minimum fluctuation value or from the minimum fluctuation value to the maximum fluctuation value (that is, a term equal to half the period); that is, the predetermined term was set to one-eighth of the period. Assuming that one cycle in two ways is a term P, pupil diameter values obtained in a term from time (3/8)P to time (4/8)P are used to calculate an average and pupil diameter values obtained in a term from time (7/8)P to time (8/8)P are also used to calculate an average.

The CPU 401 compares the calculated average pupil diameter value with the period of the fluctuation cycle in the autonomic nerves at rest. If the average pupil diameter value is smaller than the period of the fluctuation cycle in the autonomic nerves at rest, the CPU 401 creates a control command (that is, a control signal) to rotate a DC motor 804 in the normal direction. By contrast, if the average pupil diameter value is larger than the period of the fluctuation cycle in the autonomic nerves at rest, the CPU 401 creates a control command (that is, a control signal) to rotate the DC motor 804 in the reverse direction. Both control signals can include a signal that controls the rotational speed of the DC motor 804 and a term during which it rotates.

The wireless communication circuit 404 transmits and/or receives information by wireless according to a predetermined communication protocol. In this embodiment, the wireless communication circuit 404 transmits control signals created by the CPU 401. These control signals are received by a wireless communication circuit 801 included in the feedbacker 8, which will be described next.

The feedbacker 8 includes, for example, the wireless communication circuit 801, a buffer 802, a microcontroller 803, and the DC motor 804. These components implement the object driver 7 illustrated in FIG. 1.

The feedbacker 8 can be implemented as a radio-controlled model car that receives a control signal by wireless from, for example, the outside, and rotates the DC motor 804 in response to the control signal so as to drive the wheels and move the radio-controlled model car. The feedbacker 8 is formed by mounting the object driver 7 in the cabinet of the radio-controlled model car used as the object 2.

The wireless communication circuit 801 transmits and/or receives information by wireless according to a predetermined communication protocol. In this embodiment, the wireless communication circuit 801 receives control signals created by the CPU 401. The wireless communication circuit 801 sends a command indicated by a received control signal to the buffer 802. The buffer 802 stores the command.

The microcontroller 803 reads out commands stored in the buffer 802 in succession and executes these commands. If, for example, the microcontroller 803 executes a command to rotate the DC motor 804 in the normal direction, the microcontroller 803 makes the radio-controlled model car advance by controlling a current and/or a voltage to be supplied to the DC motor 804 so that the DC motor 804 rotates in the normal direction. Thus, the radio-controlled model car moves away from the user 1.

If the microcontroller 803 executes a command to rotate the DC motor 804 in the reverse direction, the microcontroller 803 backs up the radio-controlled model car by controlling a current and/or a voltage to be supplied to the DC motor 804 so that the DC motor 804 rotates in the reverse direction. Thus, the radio-controlled model car moves toward the user 1.

In addition to the rotational direction of the DC motor 804, its rotational speed and a term during which the DC motor 804 rotates are determined by control signals. Accordingly, it is possible to reciprocate the radio-controlled model car at a desired speed and in a desired period.

If the microcontroller 803 executes a command to stop the rotation of the DC motor 804, the microcontroller 803 shuts down or gradually reduces the current and/or voltage supplied to the DC motor 804. Thus, the radio-controlled model car stops moving.

An arrangement may be made so that when the DC motor 804 rotates in the normal direction, the radio-controlled model car moves toward the user 1 and that when DC motor 804 rotates in the reverse direction, the radio-controlled model car moves away from the user 1.

An object to move the radio-controlled model car toward the user 1 is to have the gazing user 1 cause convergence reflection as described above. By contrast, an object to move the radio-controlled model car away from the user 1 is to alleviate the convergence reflection caused in the user 1 as described above.

In the description with reference to FIG. 2, two semiconductor circuits, which are the CPU 401 and microcontroller 803, have been used, but this is just an example. Any circuit that can execute processing in response to a predetermined command can be used without being limited to the CPU 401 and microcontroller 803.

FIG. 4 is a flowchart indicating a procedure for processing executed by the CPU 401 that operates as an implementation of the pupil diameter calculator 4 and object position controller 5.

In step S1, the CPU 401 receives pupil image data from the camera 302 in the imaging device 3 and stores the data in the memory 402.

In step S2, the CPU 401 reads out the pupil image data from the memory 402, sends the read-out pupil image data to the image processing circuit 403, and commands the image processing circuit 403 to calculate the value of the pupil diameter. The image processing circuit 403 calculates the value of the pupil diameter in response to this command, and accumulates the calculation result (that is, pupil diameter data) in the memory 402.

In step S3, the CPU 401 references the memory 402 and obtains information about the number of pupil diameter data items accumulated in the memory 402.

In step S4, the CPU 401 decides whether a predetermined number of pupil diameter values are stored in the memory 402. If pupil diameter values are stored in the memory 402 by the predetermined number, processing proceeds to step S5. If not, processing returns to step S1. The number of predetermined values indicates a certain number of pupil diameter values obtained in a predetermined term. Processing in step S1 is also performed while processing in steps S2 to S4 is being performed. When processing branches from step S4 and step S2 is executed again, the CPU 401 perform processing by using pupil image data that was newly obtained after the previous execution of step S2.

In step S5, the CPU 401 calculates an average PDave from the predetermined number of pupil diameter values.

In step S6, the CPU 401 compares the average PDave with the at-rest average pupil diameter value PDconst. If the average PDave is larger than the at-rest average pupil diameter value PDconst, processing proceeds to step S7. If not, processing proceeds to step S8.

In step S7, the CPU 401 creates a control signal that rotates the DC motor 804 included in the feedbacker 8 in the normal direction for a certain time. In step S8B, the CPU 401 creates a control signal that rotates the DC motor 804 in the reverse direction for a certain time.

In step S9, the CPU 401 sends the created control signal to the wireless communication circuit 801 in the feedbacker 8 through the wireless communication circuit 404. Thus, the microcontroller 803 in the feedbacker 8 can rotate the DC motor 804 in the normal direction to make the object 2 advance or in the reverse direction to back up the object 2. The control signal to make the object 2 advance and the control signal to back up the object 2 do not necessarily have to be different signals. For example, a command to rotate the DC motor 804 in the normal direction only in the first half of the feedback period and to rotate the DC motor 804 in the reverse direction only in the latter half of the feedback period may be sent as a single control signal if the microcontroller 803 can interpret the control signal. After the period in which the pupil diameter changes has stabilized, steps S1 to S6 may be omitted and steps S7 and S8 may be alternately repeated.

If, for example, direct memory access (DMA) technology is used, step S1 described above may not be executed by the CPU 401 itself.

The computer program 406 described above can be recorded in a compact disc-read-only memory (CD-ROM) or another recording medium and can be placed on the market as a product. Alternatively, the computer program 406 can be transmitted through the Internet or another electronic communication line.

Results in experiments conducted by the present inventor will be specifically described below.

An LED that emits light with a wavelength of 890 nm was used as the near-infrared light source 301. One AAA battery was used as the power supply of the LED. A resistor with a resistance of 1 ohm was connected in series with the battery to adjust a voltage. A compact camera (such as, for example, KTUSCM002 from KT System Inc.) with a universal serial bus (USB) connector, the camera operating at 30 Hz, was used a camera 302 that photographs the pupil. The user 1 was asked to wear a cap. The compact camera, LED, and power supply were fixed to the cap. The compact camera was connected to a personal computer (PC) with a USB cable. Through the USB cable, power was supplied and data was transferred.

The pupil diameter calculator 4 and object position controller 5 were implemented by a PC. A computer program that operates the CPU 401 and image processing circuit 403 was installed in the PC. The object 2 was a radio-controlled model car, which was structured so as to move fore and aft with a DC motor and wheels. The microcontroller 803 and wireless communication circuit 801 were mounted on the radio-controlled model car. The DC motor 804 was controlled by the microcontroller 803. The wireless communication circuit 404 was disposed in the PC so that control signals can be sent from the wireless communication circuit 404 to the wireless communication circuit 801.

Fluctuations in the pupil diameter at rest were measured in advance. From measurement results, it was decided to change the pupil diameter in a period of 11 seconds. That is, the feedback period was set to 11 seconds. A time taken to move the radio-controlled model car toward the user 1 was set to 5.5 seconds, which is half the feedback period. A time taken to move the radio-controlled model car away from the user 1 was also set to 5.5 seconds. The algorithm for this is as described in steps S6 to S8 in FIG. 4.

In the exemplary experiments carried out by the present inventor, the pupil diameter in an initial state (at-rest pupil diameter) was measured for 150 seconds, after which the pupil diameter was measured for 150 seconds when biofeedback using pupil diameter fluctuations described above was carried out (the pupil diameter in this term is denoted PDFB).

Figure 5A:
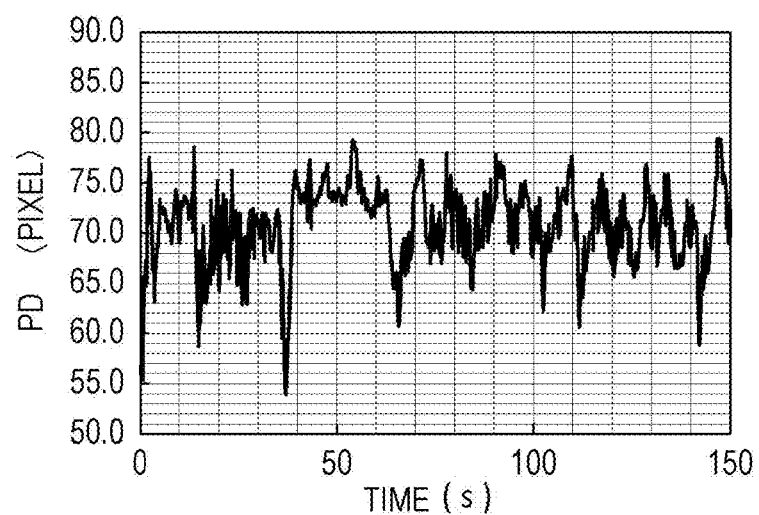
FIGS. 5A and 5B illustrate measurement results of the pupil diameter.
Figure 5B:
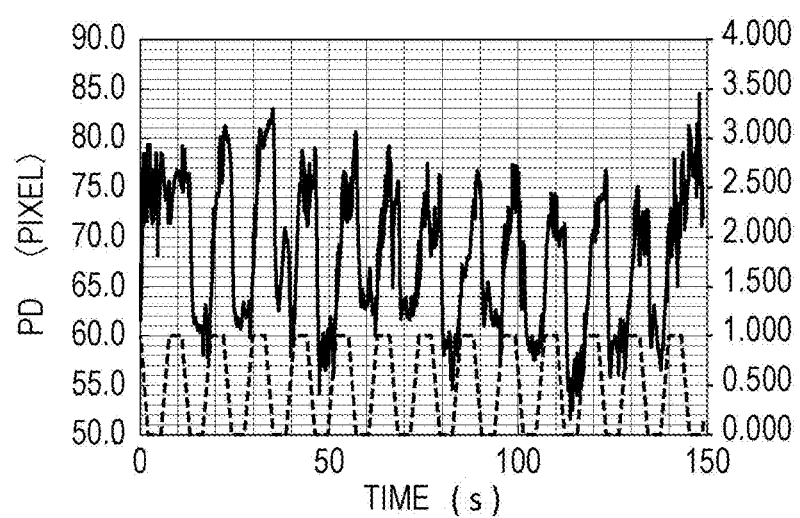

FIGS. 5A and 5B illustrate measurement results of the pupil diameter. FIG. 5A illustrates measurement results of the pupil diameter in the initial state (at-rest pupil diameter), and FIG. 5B illustrates measurement results of the pupil diameter (PDFB) when biofeedback was carried out. It is found from FIG. 5B that the diameter of the pupil of the user 1 reflects changes in the distance between the user 1 and the object 2 and that the pupil diameter noticeably changes in a period of 11 seconds due to convergence reflection.

To clarify this finding, the present inventor performed frequency analysis on the results in FIGS. 5A and 5B.

Figure 6A:
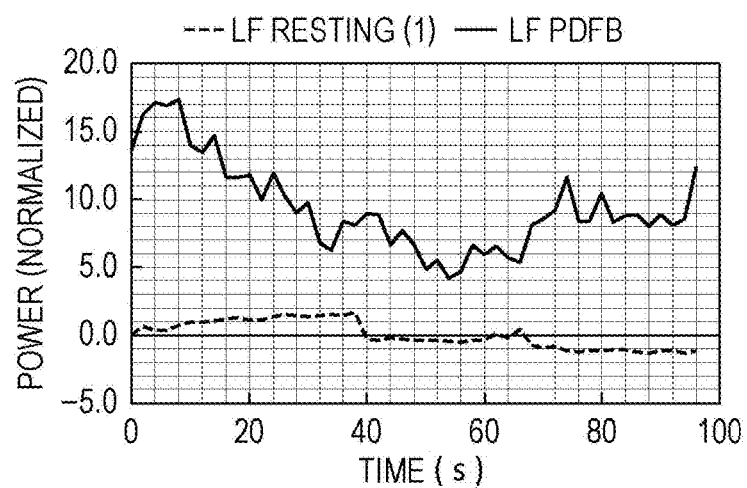
FIGS. 6A and 6B illustrate frequency analysis results.
Figure 6B:
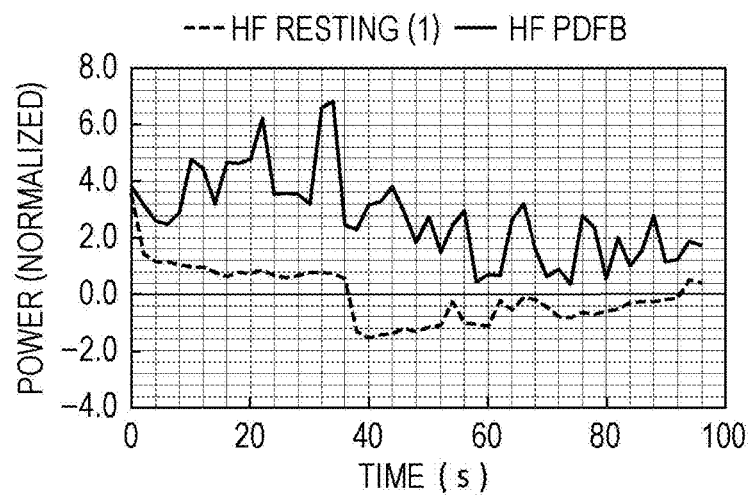

FIGS. 6A and 6B illustrate frequency analysis results. A window for 50 seconds was provided and was shifted in a period of 2 seconds to calculate a power spectrum by a Fourier transform. Numerical integration was applied to a low-frequency (LF) component at 0.04 to 0.15 Hz and a high-frequency (HF) component at 0.15 to 0.50 Hz. Furthermore, values were standardized according to the average value at rest and a standard deviation. That is, values equal to or greater than 0 indicate that fluctuations are larger than at rest, and values equal to or smaller than 0 indicate that fluctuations are smaller than at rest. The horizontal axis in FIGS. 6A and 6B indicate times at which a 50-second window started.

As illustrated in FIG. 6A, since the duration of the feedback period was 11 seconds (0.091 Hz) and the region is the LF region described above, the power of the LF component was noticeably increased. At the same time, as illustrated in FIG. 6B, the power of the HF region, which was not directly related to feedback, was also increased due to feedback. These effects were also seen in heart rate variability biofeedback. It is known that even if the period of diaphragmatic breathing is in the LF area, the HF component is also increased. That is, it can be said that results with the same tendency as in biofeedback based on heart beat fluctuations could be obtained by biofeedback based on pupil diameter fluctuations as well. It can be thought that the obtained results are due to the fact that the pupil diameter is also subject to double domination by the autonomic nerves as in heart beat fluctuations.

In biofeedback based on heart beat fluctuations, the user 1 needs to undergo the training of slow diaphragmatic breathing. In biofeedback based on pupil diameter fluctuations in the present disclosure, however, it is only necessary to simply gaze at an object that moves in synchronization with pupil diameter variations. The user 1 can periodically change the diameter of the pupil of the user 1 itself without being aware of having to change the pupil diameter. The pupil diameter is subject to double domination by the autonomic nerves as described above. Therefore, periodic variations in the pupil diameter are expected to be fed back to the autonomic nerves in the brain. As a result, it becomes possible to control the balance of the autonomic nerves.

The method in the present disclosure can be easily implemented; the user 1 does not need to undergo any special training. Biofeedback based on pupil diameter fluctuations in the present disclosure can be more reliably practiced more easily and more simply than in the conventional biofeedback based on heart beat fluctuations. The value of biofeedback based on pupil diameter fluctuations in the present disclosure is outstanding.

Second Embodiment

FIG. 7 schematically illustrates the structure of a biofeedback system 200 in this embodiment.

The biofeedback system 200 differs from the biofeedback system 100 in the first embodiment in that the biofeedback system 200 has a pupil diameter fluctuation calculator 21.

In the first embodiment, information about the autonomic nerve fluctuation period (that is, the feedback period) has been obtained in advance. In this embodiment, however, the pupil diameter fluctuation calculator 21 obtains that information.

In the description below, the same constituent elements as those described in relation to the biofeedback system 100 in FIG. 1 will be assigned the same reference numerals and their descriptions will be omitted.

The pupil diameter fluctuation calculator 21 can be implemented by using the CPU 401, memory 402, and image processing circuit 403 illustrated in FIG. 2. That is, the pupil diameter fluctuation calculator 21, pupil diameter calculator 4, and object position controller 5 are can be implemented by using common hardware. More specifically, the image processing circuit 403 calculates a plurality of pupil diameter values from a plurality of images obtained by photographing a pupil of the user 1. Then, the CPU 401 calculates the period of pupil diameter fluctuations from the plurality of pupil diameter values calculated by the image processing circuit 403. Information about the obtained period of autonomic nerve fluctuations (that is, feedback period) is stored in a resistor in the CPU 401 or in the memory 402 so that the information is used in later processing.

The operation of the pupil diameter fluctuation calculator 21 will be specifically described below.

Typically, the pupil diameter fluctuation calculator 21 operates before biofeedback is performed to obtain the period of autonomic nerve fluctuations (that is, feedback period). The imaging device 3 and pupil diameter calculator 4 operate before biofeedback is performed. The pupil diameter calculator 4 sends a signal that indicates a change in pupil diameter values to the pupil diameter fluctuation calculator 21. The pupil diameter fluctuation calculator 21 analyzes the frequency fluctuation of the signal, received from the pupil diameter calculator 4, that indicates a change in pupil diameter values. Specifically, the pupil diameter fluctuation calculator 21 calculates a power spectrum by a fast Fourier transform. In the fast Fourier transform, the present inventor used time-series information about pupil diameter values obtained over 180 seconds, as an example. Since the pupil diameter is subject to domination by the autonomic nerves as described above, pupil diameter fluctuations reflect autonomic nerve fluctuations. The pupil diameter fluctuation calculator 21 sends information about the obtained pupil diameter fluctuations to the object position controller 5.

As described in detail in relation to the first embodiment, the object position controller 5 determines, from information about pupil diameter fluctuations, a period in which to send a control signal, and periodically causes convergence reflection by moving the object 2 toward or away from the user 1.

The pupil diameter fluctuation calculator 21 may operate after biofeedback has been started. In this case, the pupil diameter fluctuation calculator 21 can change the fluctuation period while biofeedback is in progress, to move the period of the autonomic nerve fluctuations.

As described above, it becomes possible to maximize or minimize the pupil diameter fluctuations due to autonomic nerve fluctuations and to control the pupil diameter according to the state of the user 1. As a result, desired autonomic nerve control is achieved.

Third Embodiment

Figure 8:
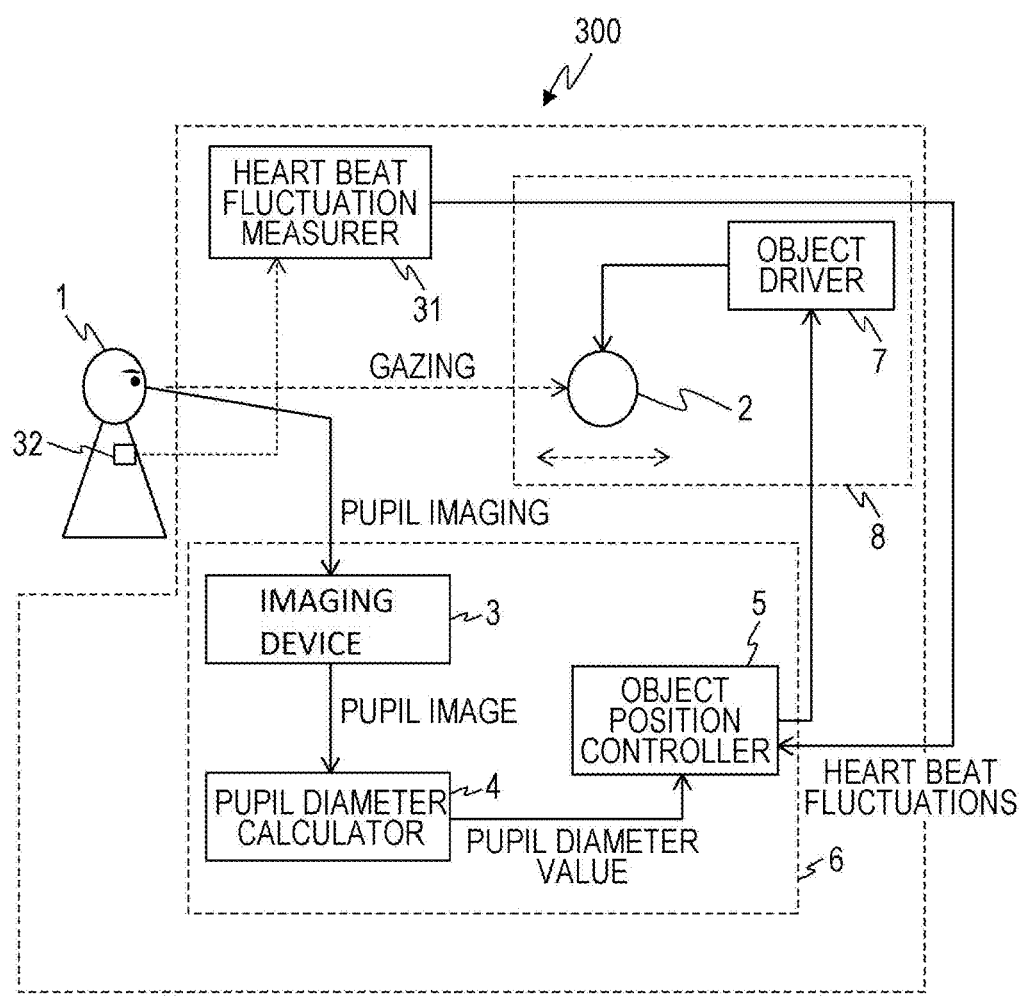
FIG. 8 schematically illustrates the structure of a biofeedback system in a third embodiment.

FIG. 8 schematically illustrates the structure of a biofeedback system 300 in this embodiment.

The biofeedback system 300 differs from the biofeedback system 100 in the first embodiment in that an electrocardiographic sensor 32 is attached to the user 1 and that a heart beat fluctuation measurer 31 is provided. In the description below, the same constituent elements as those described in relation to the biofeedback system 100 in FIG. 1 will be assigned the same reference numerals and their descriptions will be omitted.

The heart beat fluctuation measurer 31 has a communication circuit, by which a signal indicating the electrocardiogram of the user 1 is received from the electrocardiographic sensor 32 attached to the user 1 in a wireless or wired manner. The heart beat fluctuation measurer 31 can be implemented by using the CPU 401, memory 402, and wireless communication circuit 404 illustrated in FIG. 2. That is, the heart beat fluctuation measurer 31, pupil diameter calculator 4, and object position controller 5 are implemented by using common hardware.

A method will be described below by which the CPU 401, which operates as the heart beat fluctuation measurer 31, calculates heart beat fluctuations from a signal indicating electrocardiography information. The heart beat fluctuation measurer 31 obtains heart beat fluctuations by converting an electrocardiogram waveform to instantaneous heart beats.

FIGS. 9(a) to 9(e) conceptually illustrate a procedure for obtaining heart beat fluctuations from an output sent from the electrocardiographic sensor 32.

Figure 9:
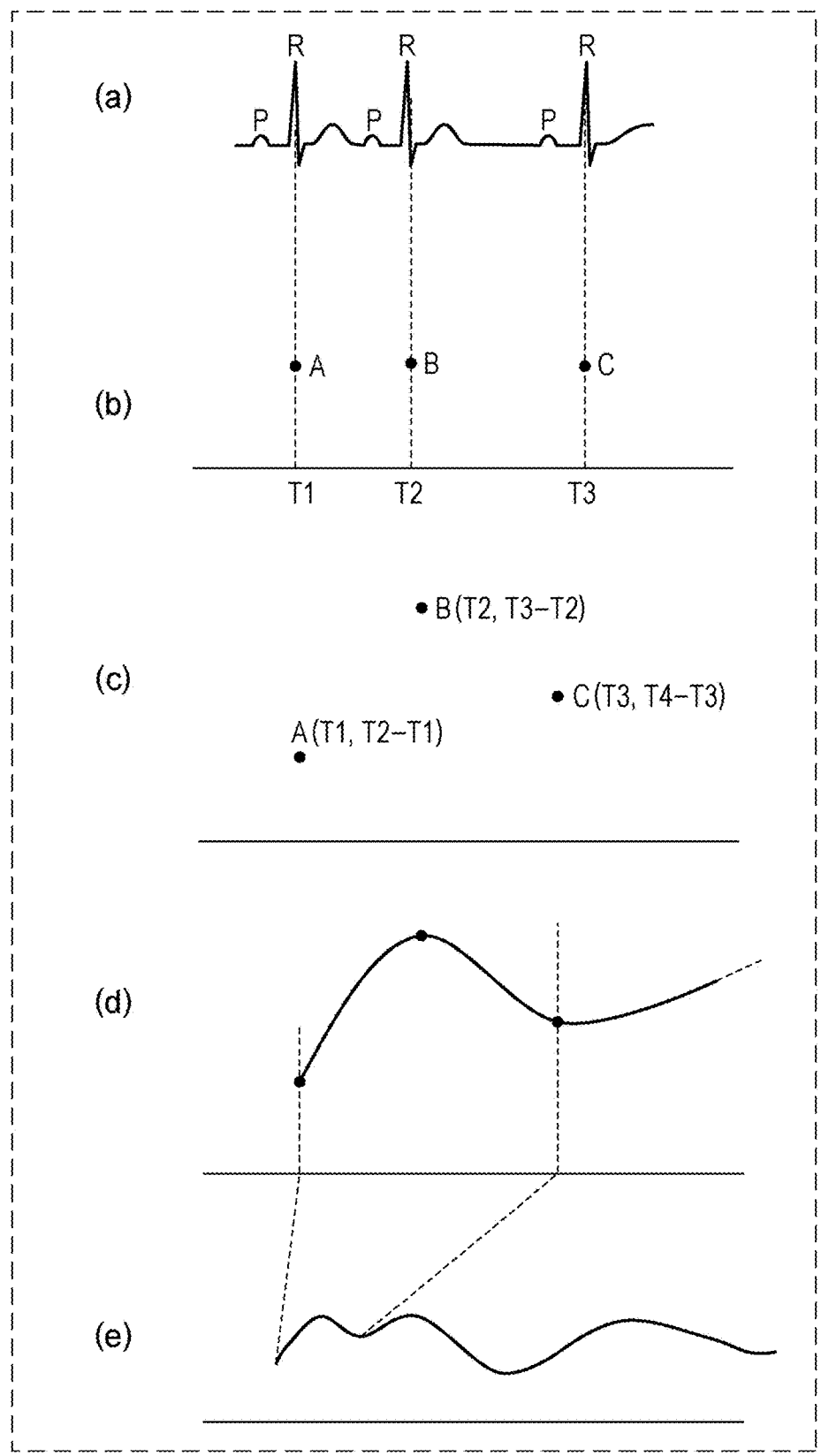
FIG. 9 conceptually illustrates a procedure for obtaining heart beat fluctuations from an output sent from an electrocardiographic sensor.

FIG. 9(a) illustrates an example of an electrocardiogram waveform output from the electrocardiographic sensor 32. The heart beat fluctuation measurer 31 receives this waveform and performs processing described below.

First, the heart beat fluctuation measurer 31 identifies the peaks of R waves of the electrocardiogram waveform. For example, the heart beat fluctuation measurer 31 identifies, as the peak of an R wave, a value that is equal to or larger than a predetermined threshold and takes a maximum value (peak). FIG. 9(b) illustrates the identified peaks of R waves together with times at which the peaks were identified.

The heart beat fluctuation measurer 31 then converts the obtained data to an R-R tachogram, that is, converts the value of the peak of each R wave indicated on the vertical axis to an R-R time interval. Specifically, the heart beat fluctuation measurer 31 replaces the value of peak A of the R wave obtained at time T1 with (T2−T1), T2 being a time at which a next peak was identified. As a result, peak A is converted to coordinates (T1, T2−T1). Similarly, the value of peak B of a second R wave obtained at time T2 is replaced with coordinates (T2, T3−T2). The value of peak C that follows is replaced with coordinates (T3, T4−T3).

FIG. 9(c) illustrates coordinates corresponding to the peaks obtained in processing described above.

The heart beat fluctuation measurer 31 smoothly interpolates the discrete coordinates obtained as described above to obtain a curve. FIG. 9(d) illustrates a curve obtained by performing spline interpolation on the coordinates in FIG. 9(c). A technology for spline interpolation is known, so its detailed description will be omitted. Interpolation processing other than spline interpolation may be used. FIG. 9(e) illustrates a curve obtained from the peaks of R waves taken over a longer time. Each curve obtained in this way is referred to as a waveform of an instantaneous heart beat.

The heart beat fluctuation measurer 31 only needs to obtain heart beat fluctuations from this type of instantaneous heart beat waveform. For example, the heart beat fluctuation measurer 31 analyzes frequency fluctuations in an instantaneous heart beat waveform. This processing is the same as processing, in the second embodiment, to analyze frequency fluctuations in a signal that indicates variations in pupil diameter values. It suffices to use a signal indicating an instantaneous heart beat waveform, instead of a signal indicating variations in pupil diameter values. Then, heart beat fluctuations can be identified.

As illustrated in FIG. 8, the heart beat fluctuation measurer 31 sends information indicating the period of the identified heart beat fluctuations to the object position controller 5.

Heart beat fluctuations are subject to domination by the autonomic nerves. Therefore, the object position controller 5 determines a period in which the object 2 is moved, in consideration of not only pupil diameter fluctuations but also information of the period of heart beat fluctuations. For example, the heart beat fluctuation measurer 31 may determine the movement period of the object 2 from the average of the period of pupil diameter fluctuations and the period of heart beat fluctuations.

Thus, it becomes possible to maximize or minimize the pupil diameter fluctuations due to autonomic nerve fluctuations and to control the pupil diameter according to the state of the user 1, as in the second embodiment. As a result, desired autonomic nerve control is achieved.

The electrocardiographic sensor 32 can be replaced with a pulse wave sensor that measures pulse waves. A pulse wave has a waveform representing a change in volume caused by a blood flow into a certain portion in body tissues, the change being captured from a body surface. A pulse wave reflects a vasomotion reaction. It is thought that when the motion of a peripheral blood vessel rather than the motion of the heart itself is measured, information having a meaning similar to an interval between R waves (that is, R-R interval) on an electrocardiogram is indirectly obtained. Therefore, a pulse wave can be processed as in processing to obtain an electrocardiogram. That is, the fluctuation period calculated according to pulse waveforms is also the period of heart beat fluctuations.

Fourth Embodiment

Figure 10:
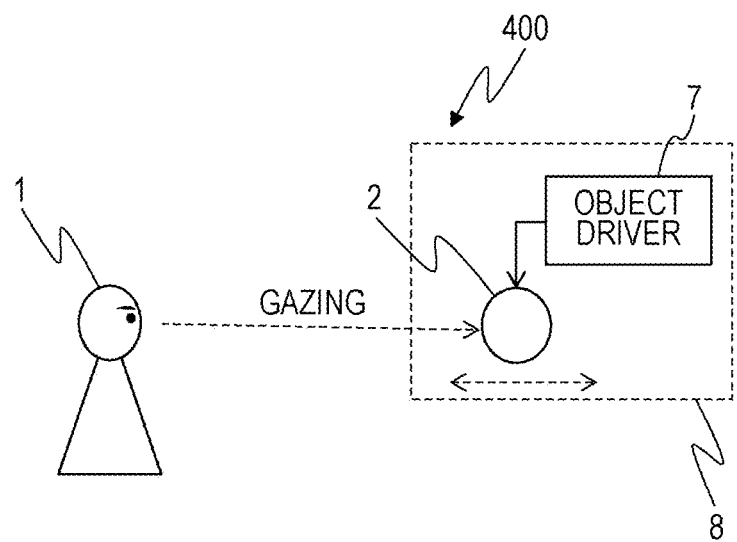
FIG. 10 schematically illustrates the structure of a biofeedback system in a fourth embodiment.
Figure 11:
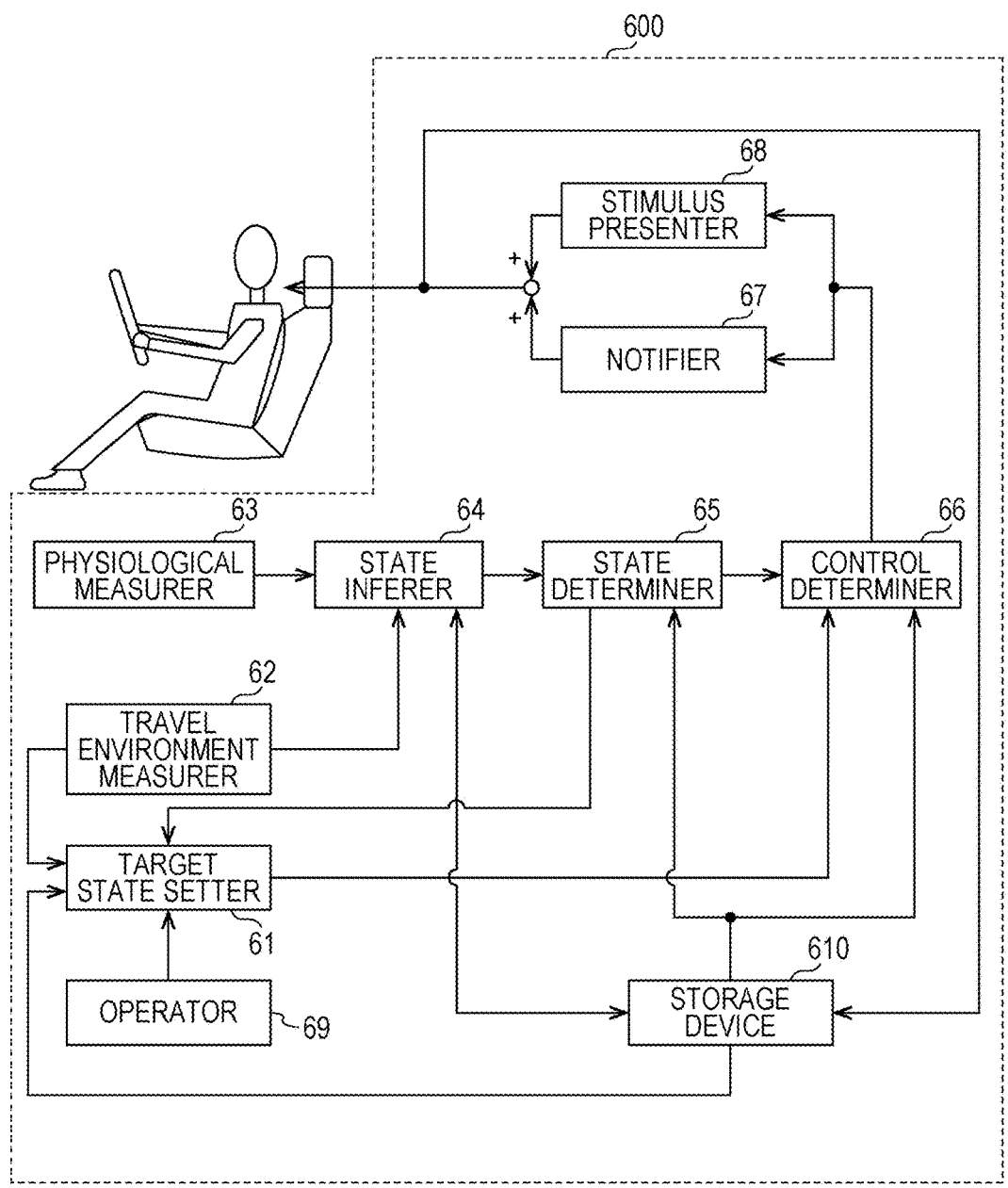
FIG. 11 illustrates a conventional biofeedback apparatus described in Japanese Unexamined Patent Application Publication No. 2008-125802.
Figure 12:
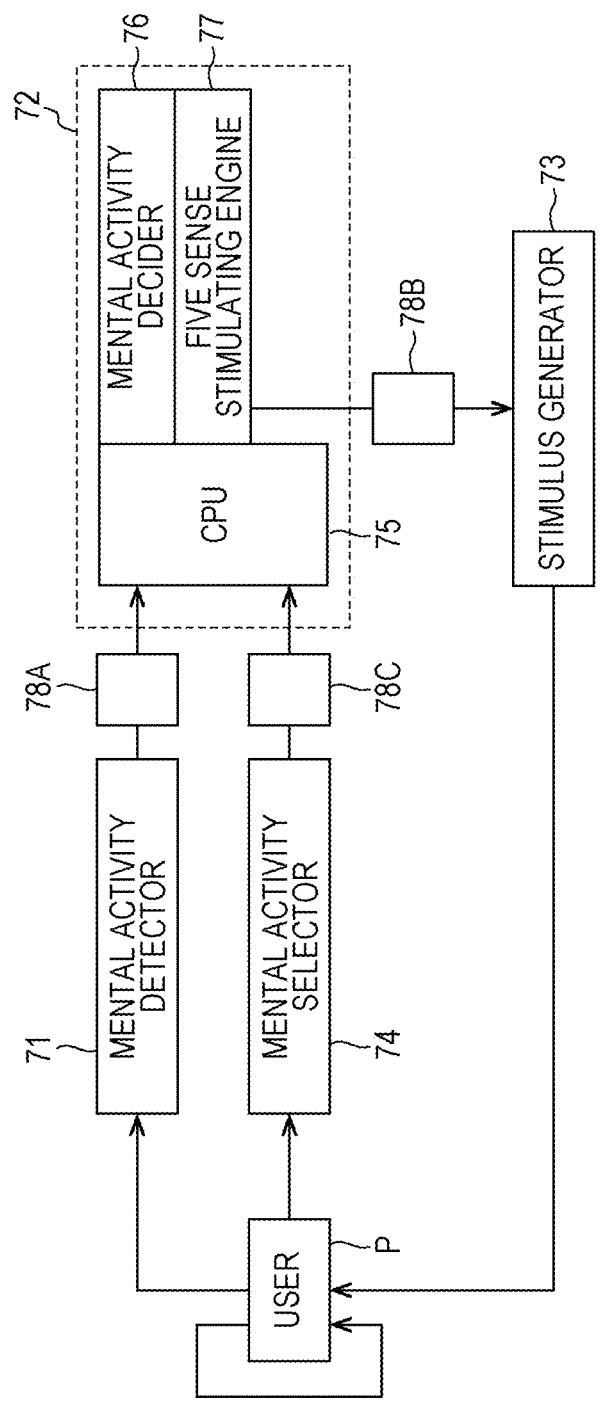
FIG. 12 illustrates a conventional biofeedback apparatus described in Japanese Unexamined Patent Application Publication No. 2001-252265.

FIG. 10 schematically illustrates the structure of a biofeedback system 400 in a fourth embodiment.

Unlike the first to third embodiments, the biofeedback system 400 in this embodiment uses only the period of autonomic nerve fluctuations of the user 1 at rest, the period having been obtained in advance, to have the object 2 continue to move fore and aft in the period of the autonomic nerve fluctuations of the user 1 at rest. In this case, the physiological signal of the user 1 does not need to be obtained, so, naturally, the period does not need to be adjusted by using the physiological signal.

That is, the biofeedback system 400 controls the movement period of the object 2 regardless of the current physiological state of the user 1 so that the pupil diameter is reduced in the period of autonomic nerve fluctuations. Information about the period of the fluctuation cycle in the autonomic nerves at rest may be obtained by, for example, the method in the second embodiment or may be obtained from heart beat fluctuations, the fluctuations being the same as pupil diameter fluctuations in that they are subject to domination by the autonomic nerves.

Hardware in the feedbacker 8, which is included in the biofeedback system 400 and has the object 2 and object driver 7, is the same as, for example, hardware in the feedbacker 8 in the biofeedback system 100 in the first embodiment, except that, since the object driver 7 does not need to receive information about the pupil diameter value unlike the first embodiment, the object driver 7 does not perform processing related to information about the pupil diameter value. The object driver 7 only needs to move the object 2 from a near position to a far position and a far position to a near position in the period of autonomic nerve fluctuations. This enables the period of the autonomic nerves to be controlled.

The difference described above appears as differences in, for example, the operation of the microcontroller 803 and information stored in the buffer 802, the microcontroller 803 and buffer 802 being illustrated in FIG. 2. The buffer 802 stores, for example, information about the period of the fluctuation cycle in the autonomic nerves of the user 1 at rest, the period having been measured in advance. The microcontroller 803 induces the point of gaze of the user 1 from a near position to a far position and from a far position to a near position by moving the object 2 on the basis of only information, stored in the buffer 802, about the period of autonomic nerve fluctuations.

In the structure in this embodiment, if the period of autonomic nerve fluctuations can be obtained as a minimum, a facility used to obtain a physiological signal from the user 1 does not need to be introduced, so the biofeedback system 400 can be very easily introduced.

The user 1 only needs to gaze at the object 2, so the user 1 does not need to master cyclic diaphragmatic breathing, which is required in heart rate variability biofeedback. Therefore, a load on the user 1 is much lighter than in heart rate variability biofeedback.

This completes the description of the exemplary embodiments of the present disclosure.

In the exemplary embodiments of the present disclosure, effects equivalent to effects in the conventional heart beat biofeedback methods are obtained by a structure and/or method that is easier, simpler, and more practical than in the conventional methods.

Variation

In the embodiments described above, a biofeedback method of moving an actual object (radio-controlled model car) and a system that moves it have been described. However, this is just an example. The object referred to in this description is not limited to a tangible object, but may be an intangible object such as a point of light emitted from a laser and is projected onto a floor or wall.

Furthermore, the present inventor confirmed that even when a virtual object on a three-dimensional display is used instead of an existing object such as a radio-controlled model car, similar effects are obtained. Specifically, a three-dimensional image of an object is displayed on a screen as an object, after which the point of gaze of the user 1 is adjusted to the object by having the user 1 gaze at the object. Then, the size of the object displayed on the screen is changed. If, for example, the size of the object displayed on the screen is changed so as to be reduced, the same effect is obtained as when the object is virtually moved from a position close to the user 1 to a position far from the user 1. Conversely, if the size of the object displayed on the screen is changed so as to be increased, the same effect is obtained as when the object is virtually moved from a position far from the user 1 to a position close to the user 1.

Furthermore, at least two lamps, for each of which a time at which the lamp is turned on can be individually set, are attached at positions apart from the user 1 by different distances, instead of a self-propelled object. The user 1 is commanded to gaze at a turned-on lamp. The lamp to be turned on is changed from the lamp at a position close to the user 1 to the lamp at a position far from the user 1. Thus, the same effect is obtained as when an object is moved from a position close to the user 1 to a position far from the user 1. Conversely, when the lamp to be turned on is changed from the lamp at a position far from the user 1 to the lamp at a position close to the user 1, the same effect is obtained as when an object is moved from a position far from the user 1 to a position close to the user 1.

The intensity of light incident on the eye of the user 1 may be changed in the period of autonomic nerve fluctuations. For example, the user 1 is commanded to gaze at a light, and the brightness of the light may be changed (or the light may be turned on and off) in the period of autonomic nerve fluctuations.

A command to the user 1 in the first to fourth embodiments and the variation may be made by using a commanding apparatus. The commanding apparatus includes, for example, a computer, a memory, and a display and/or speaker. The memory stores data of an image and/or voice presented to the user 1. The computer reads out the data from the memory. The computer may control the display so that an image is displayed on the display and/or may control the speaker so that a voice is output, according to the read-out data. Alternatively, a commander may give a command to the user 1.

In addition, the diameter of the pupil of the user 1 may be forcibly changed in synchronization with the period of autonomic nerve fluctuations, without using a command. For example, the brightness of a light in the room in which the user 1 is present may be changed (or the light may be turned on and off) in the period of autonomic nerve fluctuations. Furthermore, the user 1 may be made to wear a head-mounted display, and the brightness of the head-mounted display may be changed (or the head-mounted display may be turned on and off) in the period of autonomic nerve fluctuations. In these cases, the diameter of the pupil of the user 1 can be forcibly changed in synchronization with the period of autonomic nerve fluctuations, without using a command.

The present inventor confirmed that it is possible to induce the user 1 to cause convergence reflection by these methods as well. Times at which to turn on the lamps can be easily controlled by using a PC, a microcontroller, or the like. Thus, the same effects as described above can be obtained.

The pupil diameter fluctuation biofeedback method and biofeedback system in the present disclosure are effective in the detection and alleviation of stress and also effective as a method and system that are used to simply manage and alleviate stress in a personal daily life. The pupil diameter fluctuation biofeedback method and biofeedback system can also be applied to, for example, management and alleviation of the daily stress of employees at companies and members at organizations. With the method of using autonomic nerve fluctuations and the system using these fluctuations in the present disclosure, the balance of the autonomic nerves can be maintained and adjusted more simply, more easily, and more practically than in the conventional methods.

What is claimed is:

1. A method comprising:
    obtaining, by a processor and from a camera, information about a period of a fluctuation cycle in an autonomic nerve of a user; and
    causing, by the processor, to repeat, in a same period as the period of the fluctuation cycle in the autonomic nerve, a process that includes inducing a point of gaze of the user to move along an optical axis of the user in a direction away from the user, and inducing the point of gaze of the user to move along the optical axis of the user in a direction to approach the user, according to the obtained information;
    wherein
        the period of the fluctuation cycle in the autonomic nerve is a period of a fluctuation cycle in a diameter of a pupil of the user.

2. The method according to claim 1, wherein the period of the fluctuation cycle in the diameter of the pupil is a period corresponding to a peak frequency in a predetermined frequency band included in the fluctuation in the diameter of the pupil of the user at rest.

3. The method according to claim 1, wherein the period of the fluctuation cycle in the autonomic nerve further includes a fluctuation cycle in a heart beat of the user.

4. The method according to claim 3, wherein the period of the fluctuation cycle in the heart beat is a period corresponding to a peak frequency in a predetermined frequency band included in the fluctuation in the heart beat of the user at rest.

5. The method according to claim 1, wherein the causing to repeat includes
    adjusting the point of gaze of the user to an object by having the user gaze at the object, and
    alternately repeating, after the point of gaze is adjusted, a motion of the object in the direction away from the user, and a motion of the object in the direction to approach the user.

6. The method according to claim 1, wherein the causing to repeat includes
    displaying a three-dimensional image of an object on a screen of a display device,
    adjusting the point of gaze of the user to the object by having the user gaze at the object, and
    alternately repeating, after the point of gaze is adjusted, a virtual motion of the object in the direction away from the user, and a virtual motion of the object in the direction to approach the user by changing a size of the object.

7. The method according to claim 1, wherein the causing to repeat includes
    adjusting the point of gaze of the user to a position illuminated by light by having the user gaze at the position illuminated by the light, and
    alternately repeating, after the point of gaze is adjusted, a movement of the position illuminated by the light in the direction away from the user, and a movement of the position illuminated by the light in the direction to approach the user.

8. The method according to claim 1, wherein the causing to repeat includes
    placing a first lamp and a second lamp at positions apart from the user by different distances,
    turning on the first lamp, and adjusting the point of gaze of the user to the first lamp that is turned on by having the user gaze at the first lamp that is turned on, and
    alternately turning on, after the turning on the first lamp, the second lamp when the first lamp is turned off, and turning on, after the turning on the second lamp, the first lamp when the second lamp is turned off.

9. The method according to claim 1, further comprising:
photographing the pupil of the user while performing the causing to repeat, and calculating a value of the diameter of the pupil from one or a plurality of images obtained by photography, and
adjusting, according to the calculated value, a range within which the point of gaze of the user moves.

10. The method according to claim 9, further comprising preparing, before the causing to repeat, a target value of the diameter of the pupil, wherein
the adjusting includes inducing the point of gaze of the user to move in the direction to approach the user when the calculated value of the diameter of the pupil is larger than the target value, and/or, inducing the point of gaze of the user to move in a direction away from the user when the calculated value of the diameter of the pupil is smaller than the target value.

11. A system comprising:
a storage device that holds information about a period of a fluctuation cycle in an autonomic nerve of a user; and
a processor configured to cause to repeat, in a same period as the period of the fluctuation cycle in the autonomic nerve, a process that includes inducing a point of gaze of the user to move along an optical axis of the user in a direction away from the user, and inducing the point of gaze of the user to move along the optical axis of the user in a direction to approach the user, according to a control signal based on the information held in the storage device, wherein
the period of the fluctuation cycle in the autonomic nerve is a period of a fluctuation cycle in a diameter of a pupil of the user.

12. The system according to claim 11, further comprising:
an image processing circuit that calculates a plurality of values of the diameter of the pupil from a plurality of images obtained by photographing the pupil of the user with a camera, wherein
the processor calculates the period of the fluctuation cycle in the diameter of the pupil from the plurality of values of the diameter of the pupil, and stores the information about the period in the storage device.

13. The system according to claim 11, wherein the processor calculates the period of the fluctuation cycle in the diameter of the pupil from a plurality of images obtained by photographing the pupil of the user with a camera and stores the information about the period in the storage device.

14. The system according to claim 11, further comprising:
an electrocardiograph that measures an electrical waveform of the user, wherein
the processor calculates the period of the fluctuation cycle in a heart beat according to the electrocardiographic waveform of the user, and stores the information about the period in the storage device.

15. The system according to claim 11, further comprising:
an object to which the point of gaze of the user is configured to be adjusted; and
a motor that is configured to move the object in the direction away from the user and in the direction to approach the user, wherein
the processor creates the control signal according to the information held in the storage device, and
the processor is configured to cause the object to move in the same period as the period of the fluctuation cycle in the autonomic nerve, by controlling the motor in response to the control signal.

16. The system according to claim 11, further comprising:
an image processing circuit that calculates a value of the diameter of the pupil from one or more images obtained by photographing the pupil of the user with a camera while the point of gaze of the user is being induced by the processor,
wherein
the storage device further stores a target value of the diameter of the pupil,
the processor compares the calculated value of the diameter of the pupil with the target value,
when the calculated value of the diameter of the pupil is larger than the target value, the processor creates the control signal to induce the point of gaze of the user to move in the direction to approach the user,
when the calculated value of the diameter of the pupil is smaller than the target value, the processor creates the control signal to induce the point of gaze of the user to move in the direction away from the user, and
the processor is configured to cause to induce the point of gaze of the user in response to the control signal.

17. The system according to claim 11, further comprising:
wherein
processor calculates a value of the diameter of the pupil from one or more images obtained by photographing a pupil of the user with a camera while the point of gaze of the user is being induced by the processor,
the storage device further stores a target value of the diameter of the pupil,
the processor compares the calculated value of the diameter of the pupil with the target value,
when the calculated value of the diameter of the pupil is larger than the target value, the processor creates the control signal to induce the point of gaze of the user to move in the direction to approach the user,
when the calculated value of the diameter of the pupil is smaller than the target value, the processor creates the control signal to induce the point of gaze of the user to move in the direction away from the user, and
the processor is configured to cause to induce the point of gaze of the user in response to the control signal.

* * * * *